United States Patent [19]
Yasukohchi et al.

[11] Patent Number: 5,840,973
[45] Date of Patent: Nov. 24, 1998

[54] PROCESS FOR PRODUCING A POLYOXYALKYLENECARBOXYLIC ACID

[75] Inventors: Tohru Yasukohchi; Kei-ichi Maruyama, both of Kawasaki; Tsunekatsu Maruyama, Tokyo, all of Japan

[73] Assignee: NOF Corporation, Tokyo, Japan

[21] Appl. No.: 917,824

[22] Filed: Aug. 27, 1997

[30] Foreign Application Priority Data

Feb. 19, 1997 [JP] Japan ................................ 9-050984

[51] Int. Cl.$^6$ ................................ C07C 59/1245
[52] U.S. Cl. ................................ 562/583
[58] Field of Search ............................. 562/583

[56] References Cited

U.S. PATENT DOCUMENTS

| | | | |
|---|---|---|---|
| 4,002,676 | 1/1977 | Borggrefe | 562/583 |
| 4,219,672 | 8/1980 | Borggrefe | 562/583 |

FOREIGN PATENT DOCUMENTS

| | | |
|---|---|---|
| 2360868 | 6/1974 | Germany . |
| 2-256644 | 10/1990 | Japan . |

*Primary Examiner*—Paul J. Killos
*Attorney, Agent, or Firm*—Young & Thompson

[57] ABSTRACT

A process for producing a polyoxyalkylenecarboxylic acid which comprises: (A) a step of obtaining a salt of a polyoxyalkylenecarboxylic acid by reacting a polyoxyalkylene compound having hydroxyl group at one or both ends of the molecule with a salt of a halogenated acetic acid or a salt of a halogenated propionic acid in an amount of 4 to 50 mol per 1 mol of the polyoxyalkylene compound and an alkali metal hydroxide in an amount of 8 to 70 mol per 1 mol of the polyoxyalkylene compound in the presence of an organic solvent at 80° to 150° C.; (B) a step of converting the obtained salt of a polyoxyalkylenecarboxylic acid into the polyoxyalkylenecarboxylic acid by adjusting pH of the reaction mixture obtained in step (A) to 3 or less by adding an inorganic acid; (C) a step of removing byproducts and the like by washing the obtained solution containing the polyoxyalkylenecarboxylic acid with an aqueous solution of an inorganic salt; and (D) a step of removing the organic solvent and water at a decreased pressure at 50° to 120° C. and removing precipitated salts by filtration. A high purity, high molecular weight polyoxyalkylenecarboxylic acid which contains only small amounts of unreacted starting materials or byproducts can easily be obtained.

11 Claims, 5 Drawing Sheets

Result of quantitative analysis

| CH | PKNO | TIME | AREA | HEIGHT | MK | IDNO | CONC |
|---|---|---|---|---|---|---|---|
| 2 | 2 | 2.86 | 233931 | 9680 | V | | 15.3372 |
| | 3 | 8.44 | 1291322 | 11401 | | | 84.6628 |
| | | TOTAL | 1525253 | 21080 | | | 100 |

Result of quantitative analysis

| CH | PKNO | TIME | AREA | HEIGHT | MK | IDNO | CONC |
|---|---|---|---|---|---|---|---|
| 2 | 1 | 2.63 | 100585 | 5921 | | | 6.1877 |
| | 2 | 5.068 | 1524973 | 33888 | | | 93.8122 |
| | | TOTAL | 1625558 | 39809 | | | 100 |

Result of quantitative analysis

| CH | PKNO | TIME | AREA | HEIGHT | MK | IDNO | CONC |
|----|------|------|------|--------|----|----|------|
| 2 | 1 | 3.025 | 29859 | 3335 | | | 1.6563 |
| | 2 | 3.708 | 21605 | 953 | | | 1.1984 |
| | 3 | 4.413 | 72095 | 1612 | V | | 3.9991 |
| | 4 | 7.105 | 1679196 | 15956 | | | 93.1461 |
| | | TOTAL | 1802755 | 21855 | | | 100 |

Result of quantitative analysis

| CH | PKNO | TIME | AREA | HEIGHT | MK | IDNO | CONC |
|---|---|---|---|---|---|---|---|
| 2 | 1 | 3.046 | 14004 | 1916 | | | 0.8239 |
| | 2 | 3.74 | 32060 | 979 | | | 1.8862 |
| | 3 | 7.104 | 1653621 | 15889 | | | 97.2898 |
| | | TOTAL | 1699685 | 18784 | | | 100 |

Result of quantitative analysis

| CH | PKNO | TIME | AREA | HEIGHT | MK | IDNO | CONC |
|---|---|---|---|---|---|---|---|
| 2 | 1 | 2.317 | 176908 | 9139 | | | 11.4315 |
| | 2 | 2.88 | 1370637 | 47750 | V | | 88.5685 |
| | | TOTAL | 1547545 | 56889 | | | 100 |

Result of quantitative analysis

| CH | PKNO | TIME | AREA | HEIGHT | MK | IDNO | CONC |
|----|------|------|------|--------|-----|------|------|
| 2 | 1 | 2.81 | 190562 | 10283 | | | 11.3943 |
| | 2 | 3.003 | 187749 | 10153 | V | | 11.2261 |
| | 3 | 3.724 | 543372 | 17043 | V | | 32.49 |
| | 4 | 4.512 | 136051 | 3588 | V | | 8.135 |
| | 5 | 7.769 | 614694 | 4893 | | | 36.7546 |
| | TOTAL | | 1672428 | 45059 | | | 100 |

Result of quantitative analysis

| CH | PKNO | TIME | AREA | HEIGHT | MK | IDNO | CONC |
|---|---|---|---|---|---|---|---|
| 2 | 1 | 2.984 | 100453 | 5285 |  |  | 5.5497 |
|  | 2 | 3.623 | 207654 | 6159 | V |  | 11.4721 |
|  | 3 | 4.252 | 269792 | 5073 | V |  | 14.9049 |
|  | 4 | 7.053 | 1232182 | 10838 | V |  | 68.0733 |
|  | TOTAL |  | 1810081 | 27355 |  |  | 100 |

PROCESS FOR PRODUCING A POLYOXYALKYLENECARBOXYLIC ACID

FIELD OF THE INVENTION

The present invention relates to a process for producing a polyoxyalkylenecarboxylic acid. More particularly, the present invention relates to a process for producing a high purity, high molecular weight polyoxyalkylenecarboxylic acid which contains only small amount of a polyoxyalkylene compound used as a starting material and can advantageously be used as a material for drugs.

PRIOR ART OF THE INVENTION

Many attempts have heretofore been made to produce a carboxylic acid or a salt of a carboxylic acid by using a compound having hydroxyl group as a raw material. For example, a process for producing a carboxymethylated ether alcohol by reacting a mixture composed of an alcohol or an ether and a salt of chloroacetic acid with an alkali metal hydroxide in the same amount as the amount of the salt of chloroacetic acid at a temperature of 20° to 65° C. is proposed in Japanese Patent Application Laid-Open No. Showa 50(1975)-137924. A process for producing a carboxyalkyl ether compound by adding an aqueous caustic alkali solution dropwise into a mixture of a compound having an alcoholic hydroxyl group and an alkali salt of a monohalogenated lower carboxylic acid under heating at a decreased pressure to allow the dehydration reaction to take place is proposed in Japanese Patent Publication No. Showa 54(1979)-4932. A process for producing an ether carboxylic acid by alternatively adding an aqueous solution or an alcohol solution of a salt of a monohalogenated lower carboxylic acid and an aqueous caustic alkali solution dropwise to an ether alcohol in separate several portions under heating at a decreased pressure to allow the reaction to take place is proposed in Japanese Patent Application Laid-Open No. Showa 64(1989)-3146. A process for producing a salt of an ether carboxylic acid by supplying an aqueous solution of a caustic alkali to a mixture comprising an ether alcohol and a monohalogenated lower carboxylic acid under heating at a decreased pressure to allow the reaction to take place is proposed in Japanese Patent Publication Heisei 2(1990)-36585. A process for producing an ether carboxylic acid by supplying a solid alkali metal hydroxide and a salt of a monohalogenated lower carboxylic acid in the form of powder into a mixture of an ether alcohol and an organic solvent, allowing the reaction to take place to obtain a salt of an ether carboxylic acid, and then converting the salt of an ether carboxylic acid into an ether carboxylic acid by an aqueous solution of an inorganic acid is proposed in Japanese Patent Application Laid-Open No. Heisei 8(1996)-245496. A process for producing an ether carboxylic acid by adding an aqueous solution of an alkali metal hydroxide dropwise into a mixture of an ether alcohol, a salt of a monohalogenated lower carboxylic acid in the form of powder, and an organic solvent under heating at a decreased pressure, allowing the dehydration reaction to take place to obtain a salt of an ether carboxylic acid, and then converting the salt of an ether carboxylic acid into an ether carboxylic acid by an aqueous solution of an inorganic acid is proposed in Japanese Patent Application Laid-Open No. Heisei 8(1996)-245499.

Conventional processes for producing a polyoxyalkylenecarboxylic acid have a problem in that a salt of a halogenated carboxylic acid is hydrolyzed by an alkali metal hydroxide to form a salt of a hydroxycarboxylic acid, and the viscosity of the reaction system is markedly increased to decrease the efficiency of stirring, leading to decrease in the conversion and coloring of the product. Therefore, in the above processes, prevention of side reactions has been attempted by using an alkali metal hydroxide and a salt of a halogenated carboxylic acid each in only a slightly excess amount, i.e., 0.9 to 2.5 mol of an alkali metal hydroxide and 0.9 to 2.5 mol, preferably 0.9 to 1.1 mol, of a salt of a halogenated carboxylic acid per 1 mol of the polyoxyalkylene compound, and keeping the reaction temperature low. Increase in the conversion has been attempted by adding an alkali metal hydroxide as an aqueous solution and conducting the reaction while dehydration takes place or by using a solvent to increase the efficiency of stirring of the reaction system.

The above processes are considered to easily provide high purity polyoxyalkylenecarboxylic acids industrially. However, the polyoxyalkylene compounds used in the above processes as the starting materials have a hydrocarbon group having 6 or more carbon atoms and a low molecular weight, i.e., the number of addition of an alkylene oxide of 10 or less, because the produced polyoxyalkylenecarboxylic acids are mainly used as components of detergents.

High molecular weight derivatives of polyoxyalkylenecarboxylic acids containing no alkyl group or an alkyl group having 4 or less carbon atoms and having a molecular weight of 2,000 or more are recently used for chemical modification of physiologically active proteins and as a material for drugs, such as a material for a delivery system for drugs such as liposome. Therefore, a high purity, high molecular weight polyoxyalkylenecarboxylic acid containing little byproducts or unreacted raw materials has been desired.

In the case of conventional polyoxyalkylenecarboxylic acids which are used for surfactants, the concentration of hydroxyl group in the reaction system at the start of the reaction is high because a polyoxyalkylene compound used as the starting material has a low molecular weight, and the hydroxyl group has a sufficient opportunity to be brought into contact with a salt of a halogenated carboxylic acid. Therefore, a sufficient conversion can be obtained by using the polyoxyalkylene compound in an only slightly excess amount. A high purity can be obtained even when the concentration of the residual hydroxyl group in the unreacted raw material after the reaction is relatively high because the concentration of hydroxyl group at the start of the reaction is high.

However, in the case of a high molecular weight polyoxyalkylenecarboxylic acid, the opportunity of the hydroxyl group to be brought into contact with the halogenated carboxylic acid is small because the concentration of hydroxyl group at the start of the reaction is low, and it is difficult to obtain a sufficient conversion unless a halogenated carboxylic acid is used in a sufficiently large excess amount. Moreover, because the concentration of hydroxyl group at the start of the reaction is low, a high purity cannot be obtained unless the concentration of hydroxyl group in the residual unreacted raw material after the reaction is extremely decreased. From the above reasons, it is difficult to obtain a high purity, high molecular weight polyoxyalkylenecarboxylic acid by the above processes.

On the other hand, D. Coucouvanis et al. reported a process for producing a polyoxyalkylenecarboxylic acid by using a high molecular weight polyoxyalkylene compound having a molecular weight of 2,000 or more in Journal of American Chemical Society, Volume 101, No. 12, Pages 3394 to 3395 (1979). In this process, polyethylene glycol and potassium tert-butoxide were dissolved in tert-butyl alcohol, ethyl monobromoacetate was added dropwise to the solution to allow the reaction to proceed, an aqueous solution of sodium hydroxide was added to the reaction mixture for saponification to obtain a salt of a carboxylic acid, pH of the saponified product was adjusted to 2 by adding hydrochloric acid to covert the salt into a free carboxylic acid, the product was extracted with chloroform, and the solvent was removed. Franceso M. Veronese et al. reported another process in Journal of Controlled Release, Volume 10, Pages 145 to 154 (1989). In this process, polyethylene glycol monomethyl ether was dissolved in tert-butyl alcohol, potassium butoxide was added to the solution, the resultant solution was stirred for 8 hours, ethyl monobromoacetate was added dropwise to the solution to allow the reaction to proceed, an aqueous solution of sodium hydroxide was added to the reaction mixture for saponification to obtain a salt of a carboxylic acid, pH was adjusted to 2 by adding hydrochloric acid to convert the salt into a free ether carboxylic acid, the product was extracted with dichloromethane, and the solvent was removed.

These processes, however, the reaction contains the following steps: using ethyl bromoacetate for the reaction; saponifying the reaction product; converting the obtained salt into a free carboxylic acid by adding an inorganic acid; and extracting the product with chloroform or dichloromethane. Producing a polyoxyalkylenecarboxylic acid in a large scale is difficult because environmental problems, such as disposal of waste water, arise from the use of a solvent containing chlorine.

SUMMARY OF THE INVENTION

Accordingly, the present invention has an object of providing a process for easily producing a high purity, high molecular weight polyoxyalkylenecarboxylic acid which contains only a small amounts of unreacted raw materials or byproducts.

As the result of extensive studies conducted by the present inventors to achieve the above object, it was found that a high purity, high molecular weight polyoxyalkylenecarboxylic acid can easily be obtained when the conversion is increased by adding a salt of a halogenated carboxylic acid and an alkali metal compound in large excess amounts to the polyoxyalkylene compound in the presence of an organic solvent and conducting the reaction at a high temperature, and the unreacted halogenated carboxylic acid and hydroxycarboxylic acid and the like formed as byproducts are removed by washing with an aqueous solution of an inorganic salt. The present invention has been completed based on this knowledge.

The present invention provides:

(1) A process for producing a polyoxyalkylenecarboxylic acid represented by any of general formulae [6] and [7]:

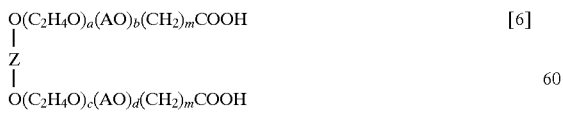

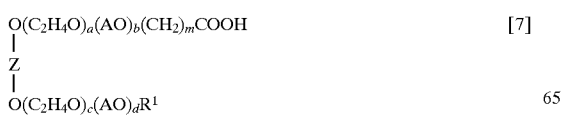

which comprises:

(A) a step of obtaining a salt of a polyoxyalkylenecarboxylic acid represented by any of general formulae [4] and [5]:

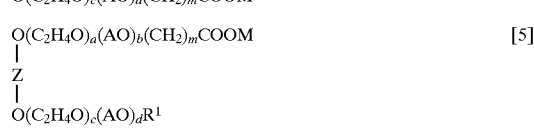

by reacting a polyoxyalkylene compound represented by any of general formulae [1] and [2]:

with a salt of a halogenated carboxylic acid represented by general formula [3]:

in an amount of 4 to 50 mol per 1 mol of the polyoxyalkylene compound and an alkali metal hydroxide in an amount of 8 to 70 mol per 1 mol of the polyoxyalkylene compound in the presence of an organic solvent in an amount by weight 0.5 to 4 times an amount by weight of the polyoxyalkylene compound at 80° to 150° C.;

(B) a step of converting the obtained salt of a polyoxyalkylenecarboxylic acid into the polyoxyalkylenecarboxylic acid by adjusting pH of the reaction mixture obtained in step (A) to 3 or less by adding an inorganic acid;

(C) a step of removing unreacted raw materials, byproducts, and the inorganic acid and the salt in excess amounts from the solution containing the polyoxyalkylenecarboxylic acid which is obtained in step (B) by washing with a 1 to 30% by weight aqueous solution of an inorganic salt 1 to 5 times at 60° to 120° C.; and (D) a step of removing the organic solvent and water from the solution obtained in step (C) at a decreased pressure at 50° to 120° C. and removing precipitated salts by filtration;

wherein, in general formulae [1] to [7], $R^1$ represents a hydrocarbon group having 1 to 4 carbon atoms; Z represents ethylene group, propylene group, or trimethylene group; AO represents an oxyalkylene group having 3 or 4 carbon atoms; a and c each represents an average number of addition of oxyethylene group, and a+c=40 to 1,000; b and d each represents an average number of addition of an oxyalkylene group having 3 or 4 carbon atoms, and b+d=0 to 100; (b+d)/(a+b+c+d)≦0.5; when b+d is 2 or more, oxyethylene group and the oxyalkylene group having 3 or 4 carbon atoms are arranged in a random order or in blocks; X represents chlorine or bromine; m represents 1 or 2; and M represents sodium or potassium;

(2) A process described in (1), wherein after step (A) has been completed, step (E) is conducted in which the organic solvent and water are removed from the reaction mixture obtained in step (A) at a decreased pressure, the solvent is added again to a resultant reaction mixture, and the reaction is allowed to proceed in the obtained solution at 100° to 150° C.; and step (B) is conducted using a product of step (E) in place of the reaction mixture obtained in step (A);

(3) A process described in any of (1) and (2), wherein, after step (A) or step (E) has been completed, step (F) is conducted in which the salt of a halogenated carboxylic acid represented by general formula [3] and the alkali metal hydroxide are added to a reaction mixture obtained in step (A) or step (E), amounts by weight of the salt of a halogenated carboxylic acid and the alkali metal hydroxide being 0.1 to 0.5 times the amounts by weight of the respective compounds used in step (A), the reaction is allowed to proceed, and this procedure is repeated 1 to 6 times; and step (B) is conducted using a product of step (F) in place of the reaction mixture obtained in step (A);

(4) A process described in any of (1), (2), and (3), wherein, after step (D) has been completed, a step is conducted in which an aqueous solution of the alkali metal hydroxide in an amount by mol 1 to 2 times the amount by mol of carboxyl group in the polyoxyalkylenecarboxylic acid is added to the product of step (D), the obtained solution is heated to 50° to 150° C., water is removed from the solution at 50° to 150° C. at a decreased pressure, the salt of a halogenated carboxylic acid, the alkali metal hydroxide, and the organic solvent are added, an amount by mol of the salt of a halogenated carboxylic acid being 0.5 to 10 times the amount by mol of the polyoxyalkylenecarboxylic acid, an amount by mol of the alkali metal hydroxide being 1 to 20 times the amount by mol of the polyoxyalkylenecarboxylic acid, and an amount by weight of the organic solvent being 0.5 to 4 times the amount by weight of the polyoxyalkylenecarboxylic acid, and the reaction is allowed to proceed at 100° to 150° C.; and then steps (B), (C), and (D) are conducted again using a reaction mixture obtained in this step in place of the reaction mixture obtained in step (A);

(5) A process described in (1), wherein the alkali metal hydroxide is sodium hydroxide or potassium hydroxide;

(6) A process described in (1), wherein the organic solvent is toluene or xylene; and (7) A process described in (1), wherein the aqueous solution of an inorganic salt is an aqueous solution of sodium chloride, potassium chloride, sodium sulfate, or magnesium sulfate.

DETAILED DESCRIPTION OF THE INVENTION

Figure 1:
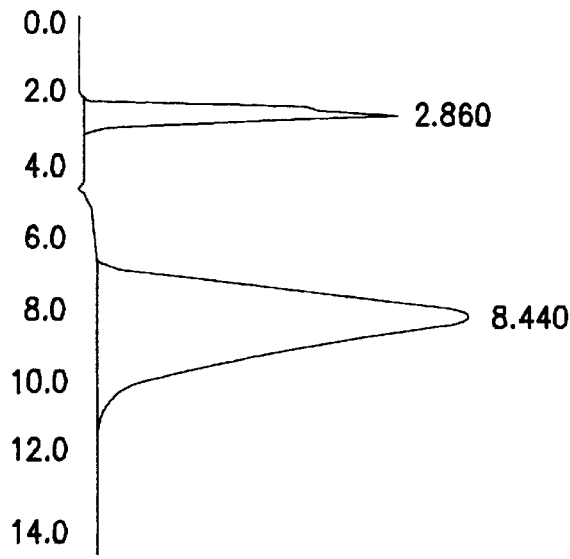
FIG. 1 shows a chromatogram of methoxypolyoxyethylenepolyoxypropyleneacetatic acid obtained in Example 1.

In the process for producing a polyoxyalkylenecarboxylic acid of the present invention, a polyoxyalkylene compound represented by general formula [1]:

or a polyoxyalkylene compound represented by general formula [2]:

is used as the starting material. In general formulae [1] and [2], $R^1$ represents a hydrocarbon group having 1 to 4 carbon atoms; Z represents ethylene group, propylene group, or trimethylene group; AO represents an oxyalkylene group having 3 or 4 carbon atoms; a and c each represents an average number of addition of the oxyethylene group, and a+c=40 to 1,000; b and d each represents an average number of addition of the oxyalkylene group having 3 or 4 carbon atoms, and b+d=0 to 100; (b+d)/(a+b+c+d)≦0.5, preferably (b+d)/(a+b+c+d)<0.3; and when b+d is 2 or more, the oxyethylene group and the oxyalkylene group having 3 or carbon atoms are arranged in a random order or in blocks.

In general formula [2], examples of the hydrocarbon group having 1 to 4 carbon atoms which is represented by $R^1$ include methyl group, ethyl group, propyl group, isopropyl group, butyl group, isobutyl group, sec-butyl group, and t-butyl group. In general formulae [1] and [2], examples of the oxyalkylene group having 3 or 4 carbon atoms which is represented by AO include oxypropylene group, oxybutylene group, oxytrimethylene group, and oxytetramethylene group.

In general formula [1] and [2], when a+c which is the total number of addition of the oxyethylene group is less than 40, there is the possibility that the affinity of the polyoxyalkylenecarboxylic acid with a living body is insufficient. When a+c exceeds 1,000, there is the possibility that the polyoxyalkylenecarboxylic acid is trapped in a living body because of an excessive affinity to cause difficulty in excretion, and the polyoxyalkylenecarboxylic acid is not suitable for drugs.

In general formulae [1] and [2], when b+d which is the total number of addition of the oxyalkylene group having 3 or 4 carbon atoms exceeds 100 or (b+d)/(a+b+c+d) exceeds 0.5, there is the possibility that the lipophilic property of the polyoxyalkylenecarboxylic acid is enhanced, and the affinity with a living body is decreased. The freezing point of the polyoxyalkylenecarboxylic acid can be decreased by the presence of the polyoxyalkylene group having 3 or 4 carbon atoms.

The process for producing the polyoxyalkylene compound represented by general formula [1] which is used in the present invention is not particularly limited. For example, the polyoxyalkylene compound can be obtained by copolymerizing ethylene oxide and an alkylene oxide having 3 or 4 carbon atoms, an oxetane having 3 or 4 carbon atoms, or tetrahydrofuran in the presence of a glycol, such as ethylene glycol, propylene glycol, trimethylene glycol, diethylene glycol, dipropylene glycol, and triethylene glycol, to form a random or block addition polymer which is bonded to the glycol. The process for producing the polyoxyalkylene compound represented by general formula [2] is not particularly limited. For example, the polyoxyalkylene compound can be obtained by copolymerizing ethylene oxide and an alkylene oxide having 3 or 4 carbon atoms, an oxetane having 3 or 4 carbon atoms, or tetrahydrofuran in the presence of an alcohol, such as methanol, ethanol, propanol, isopropanol, or butanol, to form a random or block addition polymer which is bonded to the alcohol.

In the process of the present invention, the polyoxyalkylene compound represented by general formula [1] or [2] is reacted with a salt of a halogenated carboxylic acid represented by general formula [3]:

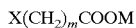
                                  [3]

In general formula [3], X represents chlorine or bromine, m represents 1 or 2, and M represents sodium or potassium. Examples of the salt of a halogenated carboxylic acid represented by general formula [3] include sodium monochloroacetate, potassium monochloroacetate, sodium monobromoacetate, potassium monobromoacetate, sodium α-monochloropropionate, potassium α-monochloropropionate, sodium α-monobromopropionate, potassium α-monobromopropionate, sodium β-monochloropropionate, potassium β-monochloropropionate, sodium β-monobromopropionate, and potassium β-monobromopropionate.

In step (A) of the process of the present invention, the salt of a halogenated carboxylic acid represented by general formula [3] and an alkali metal hydroxide are added to the polyoxyalkylene compound represented by general formula [1] or [2], and the reaction is allowed to proceed in the presence of a solvent. Examples of the used alkali metal hydroxide include lithium hydroxide, sodium hydroxide, potassium hydroxide, and rubidium hydroxide. Among these alkali metal hydroxides, sodium hydroxide and potassium hydroxide are preferably used. Examples of the used organic solvent include benzene, toluene, xylene, ethylbenzene, solvent naphtha, perchloroethylene, and monochlorobenzene. Among these organic solvent, toluene and xylene are preferably used.

In the process of the present invention, 4 to 50 mol, preferably 6 to 30 mol, of the salt of a halogenated carboxylic acid represented by general formula [3] is added to 1 mol of the polyoxyalkylene compound represented by general formula [1] or [2], and the reaction is allowed to proceed. When the amount of the salt of a halogenated carboxylic acid is less than 4 mol per 1 mol of the polyoxyalkylene compound, there is the possibility that the reaction does not proceed sufficiently, and obtaining the desired salt of a polyoxyalkylenecarboxylic acid with a high conversion becomes difficult. When the amount of the salt of a halogenated carboxylic acid exceeds 50 mol per 1 mol of the polyoxyalkylene compound, there is the possibility that a salt of a hydroxycarboxylic acid formed as a byproduct is increased, and the number of repeated washing in step (C) must be increased to remove the byproduct. Therefore, the process is industrially disadvantageous.

In the process of the present invention, 8 to 70 mol, preferably 12 to 60 mol, of the alkali metal hydroxide per 1 mol of the polyoxyalkylene compound is added in the reaction of the polyoxyalkylene compound represented by general formula [1] or [2] with the salt of a halogenated carboxylic acid represented by general formula [3]. When the amount of the alkali metal hydroxide is less than 8 mol per 1 mol of the polyoxyalkylene compound, there is the possibility that the reaction does not proceed sufficiently, and obtaining the desired salt of a polyoxyalkylenecarboxylic acid with a high conversion becomes difficult. When the amount of the alkali metal hydroxide exceeds 70 mol per 1 mol of the polyoxyalkylene compound, the conversion is not increased to the degree expected from the increased amount, and the amount of an inorganic acid necessary for adjusting pH to 3 or less in step (B) is increased. Therefore, such an amount is industrially disadvantageous. The alkali metal hydroxide is added in the form of a solid, such as granules and flakes, or as an aqueous solution.

In the process of the present invention, the reaction of the polyoxyalkylene compound represented by general formula [1] or [2] and the salt of a halogenated carboxylic acid represented by general formula [3] is conducted in the presence of an organic solvent in an amount by weight 0.5 to 4 times the amount by weight of the polyoxyalkylene compound. When the amount by weight of the organic solvent is less than 0.5 times the amount by weight of the polyoxyalkylene compound, there is the possibility that obtaining the desired salt of a polyoxyalkylenecarboxylic acid with a high conversion becomes difficult because the viscosity of the reaction system is increased to decrease the efficiency of stirring. When the amount by weight of the organic solvent exceeds 4 times the amount by weight of the polyoxyalkylene compound, the concentration of hydroxyl group of the polyoxyalkylene compound in the reaction system is decreased, and there is the possibility that the reaction rate is decreased.

In the process of the present invention, the reaction of the polyoxyalkylene compound represented by general formula [1] or [2] and the salt of a halogenated carboxylic acid represented by general formula [3] is conducted at 80° to 150° C., preferably at 100° to 140° C. When the reaction temperature is lower than 80° C., there is the possibility that obtaining the desired salt of a halogenated polyoxyalkylenecarboxylic acid becomes difficult because the reaction rate is decreased and the viscosity of the reaction system is increased to decrease the efficiency of stirring. When the temperature exceeds 150° C., there is the possibility that the polyoxyalkylene compound used as the starting material is degraded by heat, and decomposition products are formed.

In the process of the present invention, the entire amounts of the salt of a halogenated carboxylic acid and the alkali metal hydroxide may be added together to the polyoxyalkylene compound, or the salt of a halogenated carboxylic acid and the alkali metal hydroxide may be added to the polyoxyalkylene compound in several separate portions. When the salt of a halogenated carboxylic acid and the alkali metal hydroxide are added in several separate portions, 4 mol or more of the salt of a halogenated carboxylic acid and 8 mol or more of the alkali metal hydroxide per 1 mol of the polyoxyalkylene compound are preferably used in the first addition of these compounds. The amounts by weight of these compounds used in every subsequent addition are preferably 0.1 to 0.5 time, more preferably 0.2 to 0.35 times, the amounts by weight of the respective compounds used in the first addition. It is preferable that the salt of a halogenated carboxylic acid and the alkali metal hydroxide are simultaneously added.

By the reaction of the polyoxyalkylene compound represented by general formula [1] or [2] with the salt of a halogenated carboxylic acid represented by general formula [3], a salt of a polyoxyalkylenecarboxylic acid represented by general formula [4]:

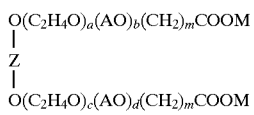

$$O(C_2H_4O)_a(AO)_b(CH_2)_mCOOM \quad [4]$$
$$|$$
$$Z$$
$$|$$
$$O(C_2H_4O)_c(AO)_d(CH_2)_mCOOM$$

or a salt of a polyoxyalkylenecarboxylic acid represented by general formula [5]:

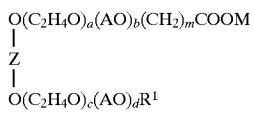

$$O(C_2H_4O)_a(AO)_b(CH_2)_mCOOM \quad [5]$$
$$|$$
$$Z$$
$$|$$
$$O(C_2H_4O)_c(AO)_dR^1$$

is obtained. In general formulae [4] and [5], $R^1$ represents a hydrocarbon group having 1 to 4 carbon atoms; Z represents ethylene group, propylene group, or trimethylene group; AO represents an oxyalkylene group having 3 or 4 carbon atoms; a and c each represents an average number of addition of the oxyethylene group, and a+c=40 to 1,000; b and d each represents an average number of addition of the oxyalkylene group having 3 or 4 carbon atoms, and b+d=0 to 100; (b+d)/(a+b+c+d)≦0.5; when b+d is 2 or more, the oxyethylene group and the oxyalkylene group having 3 or carbon atoms are arranged in a random order or in blocks; m represents 1 or 2; and M represents sodium or potassium.

When a salt of a polyoxyalkylenecarboxylic acid is prepared by the reaction of a polyoxyalkylene compound having hydroxyl group and a salt of a halogenated carboxylic acid, it is heretofore conducted that the reaction temperature is kept low and the salt of a halogenated carboxylic acid and the alkali metal hydroxide are used in small excess amounts, and the formation of a salt of a hydoxycarboxylic acid is suppressed to facilitate the purification. However, in all these conventional reactions, a low molecular weight polyoxyalkylene compound having a high concentration of hydroxyl group in the molecule is used as the starting material. When a high molecular weight polyoxyalkylene compound having a low concentration of hydroxyl group in the molecule is used as the starting material, the conversion of hydroxyl group in the polyoxyalkylene compound into a carboxyalkyl ether group cannot be increased by using a salt of a halogenated carboxylic acid and an alkali metal hydroxide in small excess amounts at a low reaction temperature. Therefore, further purification by a method, such as ion exchange, is heretofore indispensable for increasing the purity of a high molecular weight polyoxyalkylenecarboxylic acid to a level which is acceptable as a material for drugs, i.e., 80% by weight or more.

In accordance with the process of the present invention, the increase in the conversion of hydroxyl group of a polyoxyalkylene compound into a carboxyalkyl ether group is enabled by increasing the reaction temperature and using a halogenated carboxylic acid and an alkali metal hydroxide in large excess amounts, as opposed to the technical philosophy of the conventional processes. The alkali metal hydroxide in a large excess amount is converted into a salt by neutralization with an inorganic acid in step (B) and removed by washing with an aqueous solution of an inorganic salt in step (C). The salt of a hydroxycarboxylic acid which is formed in a large amount and the unreacted salt of a halogenated carboxylic acid remaining in a large amount are converted into respective free carboxylic acids in step (B) and removed by washing with an aqueous solution of an inorganic salt. Therefore, a high purity, high molecular weight polyoxyalkylenecarboxylic acid can be produced.

In step (B) of the process of the present invention, an inorganic acid is added to the reaction mixture containing the salt of a polyoxyalkylenecarboxylic acid obtained in step (A), and the salt of a polyoxyalkylenecarboxylic acid is converted into the polyoxyalkylenecarboxylic acid. Examples of the used inorganic acid include hydrochloric acid, sulfuric acid, nitric acid, and phosphoric acid. Among these acids, hydrochloric acid, sulfuric acid, and nitric acid are preferably used. pH of the reaction mixture is adjusted to 3 or less, preferably 2 or less, by adding the inorganic acid. When pH of the reaction mixture exceeds 3, there is the possibility that the salt of a polyoxyalkylenecarboxylic acid remains in the reaction mixture, and the separation in step (C) is incomplete.

In step (C) of the process of the present invention, the solution containing the polyoxyalkylenecarboxylic acid obtained in step (B) is washed with a 1 to 30% by weight aqueous solution of an inorganic salt 1 to 5 times at 60° to 120° C. to remove the unreacted materials, byproducts, and the inorganic acid and the salt in excess amounts. The aqueous solution of an inorganic salt used for the washing is not particularly limited. Examples of the aqueous solution of an inorganic salt include aqueous solutions containing ammonium chloride, lithium chloride, sodium chloride, sodium sulfate, potassium chloride, potassium nitrate, calcium chloride, calcium nitrate, magnesium sulfate, magnesium nitrate, barium chloride, beryllium sulfate, aluminum chloride, aluminum sulfate, and aluminum nitrate. Among these aqueous solutions, aqueous solutions containing sodium chloride, potassium chloride, sodium sulfate, and magnesium sulfate are preferably used.

When the concentration of the inorganic salt in the aqueous solution used for the washing in step (C) is less than 1% by weight, there is the possibility that the polyoxyalkylenecarboxylic acid is transferred into the aqueous solution of an inorganic salt, and the yield of the polyoxyalkylenecarboxylic acid is decreased. When the concentration of the inorganic salt in the aqueous solution exceeds 30% by weight, there is the possibility that the solid inorganic salt is precipitated by vaporization of water used as the solvent, and the operation of washing becomes difficult. When the temperature of washing is lower than 60° C., there is the possibility that the polyoxyalkylenecarboxylic acid is transferred into the aqueous solution of an inorganic salt, and the yield of the polyoxyalkylenecarboxylic acid is decreased. When the temperature of washing exceeds 120° C., the vapor pressure of the organic solvent present in the system is increased, and there is the possibility that the washing cannot be conducted safely.

The amount by weight of the aqueous solution of an inorganic salt used in one washing operation is preferably 0.2 to 4 times the amount by weight of the polyoxyalkylene compound used as the starting material. When the amount by weight of the aqueous solution of an inorganic salt used in one washing operation is less than 0.2 times the amount by weight of the polyoxyalkylene compound used as the starting material, there is the possibility that the efficiency of the washing is decreased, and removal of the byproducts and other impurities to achieve the desired purity becomes difficult. When the amount by weight of the aqueous solution of an inorganic salt used in one washing operation exceeds 4 times the amount by weight of the polyoxyalkylene compound used as the starting material, there is the possibility that the polyoxyalkylenecarboxylic acid is transferred into the aqueous solution of an inorganic salt, and the yield of the polyoxyalkylenecarboxylic acid is decreased. In general, the washing is sufficiently achieved when the washing operation is repeated 5 times. When the washing operation is repeated 6 times or more, there is the possibility that the amount of the polyoxyalkylenecarboxylic acid which is transferred into the aqueous solution of an inorganic salt is increased, and the yield of the polyoxyalkylenecarboxylic acid is decreased. An organic solvent may additionally be used in step (C) where necessary.

In step (D) of the process of the present invention, the organic solvent and water are removed from the solution containing the polyoxyalkylenecarboxylic acid at 50° to 120° C., preferably at 60° to 90° C. after the washing in step (C) has been completed. Salts precipitated in small amounts are then removed by filtration, and the polyoxyalkylenecarboxylic acid is obtained. The organic solvent and water is preferably removed at a decreased pressure. When the organic solvent and water are removed at a temperature lower than 50° C., there is the possibility that a long time is required for the removal, and the process becomes industrially disadvantageous. When the organic solvent and water are removed at a temperature exceeding 120° C., there is the possibility that the reaction takes place between hydroxyl group of derivatives of the unreacted polyoxyalkylene glycol which remain in the system and carboxyl group of the polyoxyalkylenecarboxylic acid, and esterification products are formed as byproducts.

In the process of the present invention, after step (A) has been completed, step (E) may be conducted in which the organic solvent and water are removed from the reaction mixture obtained in step (A) at a decreased pressure, the solvent is added again to a resultant reaction mixture, and the reaction is allowed to proceed in the obtained solution at 100° to 150° C.; and then step (B) may be conducted using the product of step (E) in place of the reaction mixture obtained in step (A). The amount by weight of the organic solvent which is added again in step (E) is preferably 0.5 to 4 times the amount by weight of the polyoxyalkylene compound used as the starting material. When the amount by weight of the solvent is less than 0.5 times the amount by weight of the polyoxyalkylene compound used as the starting material, there is the possibility that the viscosity of the reaction system is increased to decrease the efficiency of stirring, and the reaction does not proceed sufficiently. When the amount by weight of the solvent exceeds 4 times the amount by weight of the polyoxyalkylene compound used as the starting material, the concentration of the reaction system is decreased, and there is the possibility that the reaction rate is decreased. Unreacted hydroxyl group of the polyoxyalkylene compound represented by general formula [1] or [2] remains in a small amount after step (A) has been completed. The hydroxyl group of the polyoxyalkylene compound represented by general formula [1] or [2] which remains unreacted can be brought into reaction with the salt of a halogenated carboxylic acid represented by general formula [3] by removing the solvent and water by distillation, adding the solvent again, and subsequently resuming the reaction. Thus, the purity of the polyoxyalkylenecarboxylic acid can be increased further.

A In the process of the present invention, after step (A) or step (E) has been completed, step (F) may be conducted in which the salt of a halogenated carboxylic acid represented by general formula [3] and the alkali metal hydroxide are added to a reaction mixture obtained in step (A) or step (E), amounts by weight of the salt of a halogenated carboxylic acid and the alkali metal hydroxide being 0.1 to 0.5 times the amounts by weight of the respective compounds used in step (A), the reaction is allowed to proceed, and this procedure is repeated 1 to 6 times; and then step (B) may be conducted using a product of step (F) in place of the reaction mixture obtained in step (A). Unreacted hydroxyl group of the polyoxyalkylene compound represented by general formula [1] or [2] remains in a small amount after step (A) or step (E) has been completed. The hydroxyl group of the polyoxyalkylene compound represented by general formula [1] or [2] which remains unreacted can completely be converted into a carboxyalkyl ether group by adding the salt of a halogenated carboxylic acid and the alkali metal hydroxide and resuming the reaction. When the amount by weight of the salt of a halogenated carboxylic acid or the alkali metal hydroxide used in one reaction is less than 0.1 times the amount by weight of the respective compound used in step (A), there is the possibility that the reaction of the hydroxyl group which remains unreacted does not proceed sufficiently. In general, it is not necessary that the amount by weight of the salt of a halogenated carboxylic acid or the alkali metal hydroxide used in one reaction exceeds 0.5 times the amount by weight of the respective compound used in step (A) because the amount of hydroxyl group remaining unreacted is small. Repeating the reaction 6 times or less in step (F) is sufficient. The conversion into the salt of a polyoxyalkylenecarboxylic acid is hardly increased even when the reaction is repeated 7 times or more.

In the process of the present invention, after step (D) has been completed, a step may be conducted in which an aqueous solution of the alkali metal hydroxide in an amount by mol 1 to 2 times the amount by mol of carboxyl group in the polyoxyalkylenecarboxylic acid is added to the product of step (D), the obtained solution is heated to 50° to 150° C., preferably 70° to 110° C., water is removed from the solution at 50° to 150° C., preferably 80° to 120° C., at a decreased pressure, the salt of a halogenated carboxylic acid, the alkali metal hydroxide, and the organic solvent are added, an amount by mol of the salt of a halogenated carboxylic acid being 0.5 to 10 times the amount by mol of the polyoxyalkylenecarboxylic acid, an amount by mol of the alkali metal hydroxide being 1 to 20 times the amount by mol of the polyoxyalkylenecarboxylic acid, and an amount by weight of the organic solvent being 0.5 to 4 times the amount by weight of the polyoxyalkylenecarboxylic acid, and the reaction is allowed to proceed at 100° to 150° C.; and then steps (B), (C), and (D) may be conducted again using the reaction mixture obtained in this step in place of the reaction mixture obtained in step (A).

When the amount by mol of the alkali metal hydroxide added to the polyoxyalkylenecarboxylic acid is less than the amount by mol of the carboxyl group of the carboxylic acid, the carboxyl group is not completely converted into the salt, and a part of the carboxyl group remains free. Therefore, such an amount is not preferable. In general, it is not necessary that the amount by mol of the added alkali metal hydroxide exceeds 2 times the amount by mol of the carboxyl group of the polyoxyalkylenecarboxylic acid because the polyoxyalkylenecarboxylic acid in this step is already highly pure. By adding an aqueous solution of the alkali metal hydroxide to the polyoxyalkylenecarboxylic acid and heating the obtained solution to 50° to 150° C., preferably 70° to 110° C., the polyoxyalkylenecarboxylic acid is completely neutralized, and esters which may possibly be formed from the unreacted polyoxyalkylene glycol and the polyoxyalkylenecarboxylic acid in some amount as byproducts in step (D) can completely be saponified. When the heating temperature is lower than 50° C., there is the possibility that the neutralization and the saponification of the polyoxyalkylenecarboxylic acid are insufficient. When the heating temperature exceeds 150° C., there is the possibility that the polyoxyalkylenecarboxylic acid is degraded by heat. Water in the system is then removed at a decreased pressure at 50° to 150° C., preferably 80° to 120° C. When the temperature of the dehydration is lower than 50° C., there is the possibility that the dehydration is insufficient. When the temperature of the dehydration exceeds 150° C., there is the possibility that the polyoxyalkylenecarboxylic acid is decomposed by heat and degraded.

When the added amount by mol of the salt of a halogenated carboxylic acid represented by general formula [3] is less than 0.5 times the amount by mol of the salt of a polyoxyalkylenecarboxylic acid, there is the possibility that conversion of the hydroxyl group which remains unreacted into a carboxyalkyl ether is insufficient. Because the amount of the hydroxyl group which remains unreacted is small, it is generally not necessary that the salt of a halogenated carboxylic acid is added in an amount by mol exceeding 10 times the amount by mol of the salt of a polyoxyalkylenecarboxylic acid. When the added amount by mol of the alkali metal hydroxide is less than the amount by mol of the salt of a polyoxyalkylenecarboxylic acid, there is the possibility that conversion of the hydroxyl group which remains unreacted into a carboxyalkyl ether is insufficient. Because the amount of hydroxyl group which remains unreacted is small, it is generally not necessary that the alkali metal hydroxide is added in an amount exceeding 20 times the amount by mol of the polyoxyalkylenecarboxylic acid.

When the added amount by weight of the organic solvent is less than 0.5 times the amount by weight of the salt of a polyoxyalkylenecarboxylic acid, there is the possibility that the viscosity of the reaction system is increased to decrease the efficiency of stirring, and the conversion of hydroxyl group which remains unreacted into a carboxyalkyl ether is insufficient. When the amount by weight of the organic solvent exceeds 4 times the amount by weight of the salt of a polyoxyalkylenecarboxylic acid, the concentration of hydroxyl group in the reaction system is decreased, and there is the possibility that the reaction rate is decreased because the amount of hydroxyl group which remains unreacted is small. When the reaction temperature is lower than 100° C., there is the possibility that conversion of hydroxyl group which remains unreacted into a carboxyalkyl ether is insufficient because the reaction rate is small and the efficiency of stirring is decreased by the increase in the viscosity of the reaction system. When the reaction temperature exceeds 150° C., there is the possibility that the polyoxyalkylenecarboxylic acid is degraded by heat, and decomposition products are formed.

In the process of the present invention, the purity of the polyoxyalkylenecarboxylic acid can be still more increased by converting the hydroxyl group which remains in the polyoxyalkylenecarboxylic acid in a very small amount after step (D) into a carboxyalkyl ether by the following procedures: after the high purity polyoxyalkylenecarboxylic acid has been isolated in the above process, the polyoxyalkylenecarboxylic acid is converted into a salt of the polyoxyalkylenecarboxylic acid by adding an alkali metal hydroxide, followed by heating; then formed water is removed at a decreased pressure; a salt of a halogenated carboxylic acid and an alkali metal hydroxide are added to the obtained product in the presence of an organic solvent; and the reaction is allowed to proceed in the resultant mixture.

In accordance with the process of the present invention, the polyoxyalkylenecarboxylic acid represented by general formula [6]:

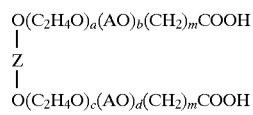

or the polyoxyalkylenecarboxylic acid represented by general formula [7]:

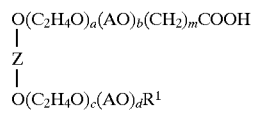

can be obtained efficiently with a high purity. In general formulae [6] and [7], $R^1$ represents a hydrocarbon group having 1 to 4 carbon atoms; Z represents ethylene group, propylene group, or trimethylene group; AO represents an oxyalkylene group having 3 or 4 carbon atoms; a and c each represents an average number of addition of the oxyethylene group, and a+c=40 to 1,000; b and d each represents an average number of addition of the oxyalkylene group having 3 or 4 carbon atoms, and b+d=0 to 100; (b+d)/(a+b+c+d) <0.5; when b+d is 2 or more, the oxyethylene group and the oxyalkylene group having 3 or carbon atoms are arranged in a random order or in blocks; and m represents 1 or 2.

In accordance with the process of the present invention, a high purity polyoxyalkylenecarboxylic acid having a molecular weight of 2,000 or more can be produced. The polyoxyalkylenecarboxylic acid containing unreacted materials or byproducts in only small amounts can advantageously be used as a material for drugs, such as a material for modification of physiologically active proteins and materials for delivery systems for drugs such as liposome.

To summarize the advantages of the present invention, in accordance with the process of the present invention, the conversion of hydroxyl group into a carboxyalkyl ether group can be increased to 80% or more in the reaction of a high molecular weight polyoxyalkylene compound and a salt of a halogenated carboxylic acid by using the salt of a halogenated carboxylic acid and an alkali metal hydroxide in large excess amounts and allowing the reaction to proceed in an organic solvent at a high temperature. Moreover, a hydroxycarboxylic acid formed as a byproduct in a large amount, the unreacted halogenated carboxylic acid, and the residual alkali metal hydroxide can be removed by washing the reaction product with an aqueous solution of an inorganic salt in the presence of an organic solvent under an acidic condition, and a high purity, high molecular weight polyoxyalkylenecarboxylic acid can be obtained with a high conversion into the carboxylic acid. In accordance with the process of the present invention, a high purity, a high molecular weight polyoxyalkylenecarboxylic acid useful as a material for drugs can easily be produced without using any specific materials, apparatuses for the reaction, or catalysts.

EXAMPLES

The present invention is described in more detail with reference to examples. However, the present invention is not limited by the examples.

In the examples, the hydroxyl value was measured in accordance with the method of Japanese Industrial Standard K 1557 6.4, and the acid value and the saponification value were measured in accordance with the method of Japanese Industrial Standard K 0070.

The purity of a product was obtained by the liquid chromatography. The conditions of the measurement of the liquid chromatography were as follows:

| | |
|---|---|
| column: | ASAHIPAK ES-502N |
| developing solvent: | |
| a 5 mM buffer solution of ammonium formate (pH:8.0) (Examples 1, 2, and 5) | |
| a 20 mM buffer solution of ammonium formate (pH:8.0) (Examples 3 and 4, and Comparative Examples 1 and 2) | |
| column oven temperature: | 30° C. |
| sample concentration: | 1 (W/V)% |
| injected amount of a sample: | 20 μl |
| flow rate: | 1.0 ml/min |

Example 1

Into a 5 liter autoclave, 1,000 g (0.5 mol) of polyoxyethylenepolyoxypropylene monomethyl ether expressed by formula [8]:

$$CH_3O[(C_2H_4O)_{38}(C_3H_6O)_5]H \qquad [8]$$

and having an average molecular weight of 2,003 and a hydroxyl value of 28.0 (the oxyethylene group and the oxypropylene group arranged in a random order) and 1,800 g of toluene were placed, and the resultant mixture was stirred under a nitrogen atmosphere at 50° C. until the polyoxyethylenepolyoxypropylene monomethyl ether was completely dissolved. Then, 505 g (9.0 mol) of potassium hydroxide in flakes and 350 g (3.0 mol) of sodium monochloroacetate were added to the solution. The autoclave was quickly purged with nitrogen and heated to 120° C. The mixture was kept being stirred at 120° C. for 5 hours to allow the reaction to proceed. The temperature was decreased to 80° C., and 500 g of ion-exchanged water was added. After being stirred for 30 minutes, the entire amount of the reaction mixture was transferred into a separation funnel. To the reaction mixture in the separation funnel, 38% by weight hydrochloric acid was slowly added to adjust pH of the reaction mixture to 2. Then, 1,000 g of a 23% aqueous solution of sodium chloride was added, and the obtained mixture was heated to 90° C. while being stirred. After the heated mixture was left standing at 90° C. for 1 hour, a separated aqueous layer was removed. The remaining toluene layer was washed with 1,000 g of a 23% by weight aqueous solution of sodium chloride 4 times in accordance with the same procedure.

The toluene layer was taken out, and water and the solvent were removed at a decreased pressure of 5 to 30 mmHg at 75°±5° C. while nitrogen gas was blown into the solution. Salts precipitated from the product were removed by filtration with pressure, and 873 g of methoxypolyoxyethylenepolyoxypropyleneacetic acid expressed by formula [9]:

$$CH_3O[(C_2H_4O)_{38}(C_3H_6O)_5]CH_2COOH \qquad [9]$$

was obtained. The obtained methoxypolyoxyethylenepolyoxypropyleneacetic acid had an acid value of 23.3 (theoretical value: 27.2), a hydroxyl value of 3.8 after correction by the acid value (theoretical value: 0), a conversion of the hydroxyl group into the carboxylic acid of 85.7% as calculated from the acid value, and a saponification value of 23.4 (theoretical value: 27.2).

The obtained methoxypolyoxyethylenepolyoxypropyleneacetic acid was analyzed by the liquid chromatography. The obtained chromatogram is shown in FIG. 1. In the chromatogram shown in FIG. 1, the peak at the retention time of 2.86 minutes is assigned to polyoxyethylenepolyoxypropylene monomethyl ether expressed by formula [8], and the peak at the retention time of 8.44 minutes is assigned to methoxypolyoxyethylenepolyoxypropyleneacetic acid expressed by formula [9]. It could be confirmed from FIG. 1 that the purity of the obtained methoxypolyoxyethylenepolyoxypropyleneacetic acid was 84.7% by weight.

Example 2

Into a 5 liter autoclave, 1,000 g (0.2 mol) of polyoxyethylene monomethyl ether expressed by formula [10]:

$$CH_3O(C_2H_4O)_{113}H \qquad [10]$$

and having an average molecular weight of 5,009 and a hydroxyl value of 11.2 and 1,800 g of xylene were placed, and the resultant mixture was stirred under a nitrogen atmosphere at 50° C. until polyoxyethylene monomethyl ether was completely dissolved. Then, 290 g (5.16 mol) of potassium hydroxide in flakes and 147 g (1.26 mol) of sodium monochloroacetate were added to the solution. The autoclave was quickly purged with nitrogen and heated to 120° C. The mixture was kept being stirred at 120° C. for 5 hours to allow the reaction to proceed. The temperature was decreased to 80° C., and 84 g (1.50 mol) of potassium hydroxide in flakes and 44 g (0.38 mol) of sodium monochloroacetic acid were added. The autoclave was quickly purged with nitrogen and heated to 120° C. The mixture was kept being stirred at 120° C. for 3 hours to allow the reaction to proceed. The temperature was decreased to 80° C. again, and 84 g (1.50 mol) of potassium hydroxide in flakes and 44 g (0.38 mol) of sodium monochloroacetic acid were added. The autoclave was quickly purged with nitrogen and heated to 120° C. The mixture was kept at 120° C. for 3 hours to allow the reaction to proceed in the same manner.

Then, the temperature was decreased to 80° C., and 500 g of ion-exchanged water was added. After being stirred for 30 minutes, the entire amount of the reaction mixture was transferred into a separation funnel. To the reaction mixture in the separation funnel, 38% by weight hydrochloric acid was slowly added to adjust pH of the reaction mixture to 1.5. Then, 500 g of a 23% aqueous solution of sodium chloride was added, and the obtained mixture was heated to 90° C. while being stirred. After the heated mixture was left standing at 90° C. for 1 hour, a separated aqueous layer was removed. The remaining xylene layer was washed with 500 g of a 23% by weight aqueous solution of sodium chloride 4 times in accordance with the same procedure.

The xylene layer was taken out, and water and the solvent were removed at a decreased pressure of 5 to 30 mmHg at 80°±5° C. while nitrogen gas was blown into the solution. Salts precipitated from the product were removed by filtration with pressure, and 791 g of methoxypolyoxyethyleneacetic acid expressed by formula [11]:

$$CH_3O(C_2H_4O)_{113}CH_2COOH \qquad [11]$$

was obtained. The obtained methoxypolyoxyethyleneacetic acid had an acid value of 10.4 (theoretical value: 11.07), a hydroxyl value of 0.6 after correction by the acid value (theoretical value: 0), a conversion of the hydroxyl group into the carboxylic acid of 93.9% as calculated from the acid value, and a saponification value of 10.4 (theoretical value: 11.07).

Figure 2:
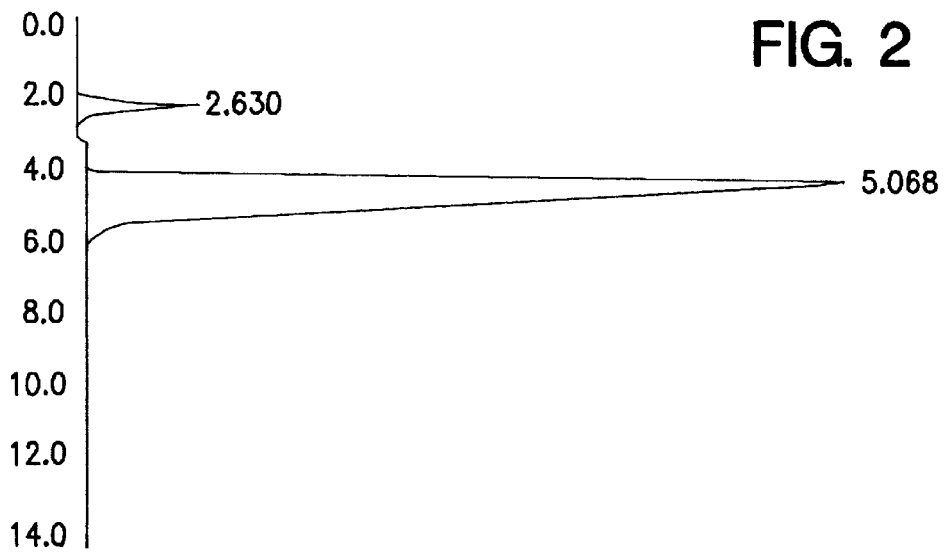
FIG. 2 shows a chromatogram of methoxypolyoxyethyleneacetic acid obtained in Example 2.

The chromatogram of methoxypolyoxyethyleneacetic acid obtained in accordance with the same method as that used in Example 1 is shown in FIG. 2. It could be confirmed from FIG. 2 that the purity of the obtained methoxypolyoxyethyleneacetic acid was 93.8% by weight.

Example 3

Into a 10 liter autoclave, 1,240 g (0.4 mol) of polyoxyethylene glycol expressed by formula [12]:

$$HO(C_2H_4O)_{70}H \qquad [12]$$

and having an average molecular weight of 3,100 and a hydroxyl value of 36.2 and 1,000 g of toluene were placed, and the resultant mixture was stirred under a nitrogen atmosphere at 50° C. until polyoxyethylene glycol was completely dissolved. Then, 348 g (8.7 mol) of sodium hydroxide in granules and 478 g (4.1 mol) of sodium monochloroacetate were added to the solution. The autoclave was quickly purged with nitrogen and heated to 130° C. The mixture was kept being stirred at 130° C. for 5 hours to allow the reaction to proceed.

Then, removal of water and the solvent was started by decreasing the pressure while the temperature was kept at 130° C. After the pressure inside the autoclave reached 30 mmHg, the autoclave was kept at the same pressure and temperature for 1 hour. The temperature was decreased to 70° C., and 104 g (2.6 mol) of sodium hydroxide in granules, 151 g (1.3 mol) of sodium monochloroacetic acid, and 2,000 g of toluene were added. The autoclave was quickly purged with nitrogen and heated to 130° C. The mixture was kept being stirred at 130° C. for 3 hours to allow the reaction to proceed. The temperature was decreased to 80° C. again, and 72 g (1.8 mol) of sodium hydroxide in granules and 96 g (0.82 mol) of sodium monochloroacetic acid were added. The autoclave was quickly purged with nitrogen and heated to 130° C. The mixture was kept being stirred at 130° C. for 3 hours to allow the reaction to proceed. The temperature was decreased to 80° C. again, and 72 g (1.8 mol) of sodium hydroxide in granules and 96 g (0.82 mol) of sodium monochloroacetic acid were added. The autoclave was quickly purged with nitrogen and heated to 130° C. The mixture was kept being stirred at 130° C. for 3 hours to allow the reaction to proceed.

Then, the temperature was decreased to 80° C., and 800 g of ion-exchanged water was added. After being stirred for 30 minutes, the entire amount of the reaction mixture was transferred into a separation funnel. To the reaction mixture in the separation funnel, 38% by weight hydrochloric acid was slowly added to adjust pH of the reaction mixture to 1.2. Then, 1,000 g of a 23% aqueous solution of sodium chloride was added, and the obtained mixture was heated to 90° C. while being stirred. After the heated mixture was left standing at 90° C. for 1 hour, a separated aqueous layer was removed. The remaining toluene layer was washed with 1,000 g of a 23% by weight aqueous solution of sodium chloride 4 times in accordance with the same procedure.

The toluene layer was taken out, and water and the solvent were removed at a decreased pressure of 5 to 30 mmHg at 80°±5° C. while nitrogen gas was blown into the solution. Salts precipitated from the product were removed by filtration with pressure, and 1,018 g of polyoxyethylenediacetic acid expressed by formula [13]:

$$HOOCCH_2O(C_2H_4O)_{70}CH_2COOH \qquad [13]$$

was obtained. The obtained polyoxyethylenediacetic acid had an acid value of 32.8 (theoretical value: 34.87), a hydroxyl value of 2.0 after correction by the acid value (theoretical value: 0), a conversion of the hydroxyl group into the carboxylic acid of 94.0% as calculated from the acid value, and a saponification value of 33.1 (theoretical value: 34.87).

Figure 3:
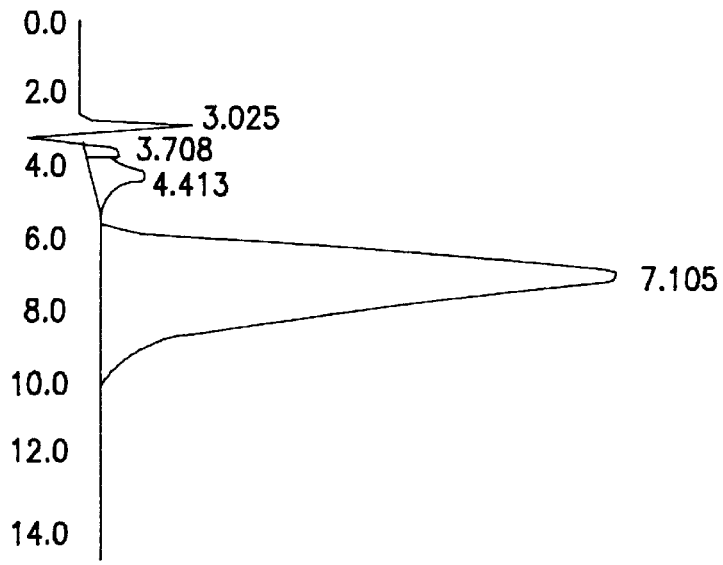
FIG. 3 shows a chromatogram of polyoxyethylenediacetic acid obtained in Example 3.

The chromatogram of polyoxyethylenediacetic obtained in accordance with the same method as that used in Example 1 except that a 20 mM buffer solution of ammonium formate was used as the developing solvent is shown in FIG. 3. It could be confirmed from FIG. 3 that the purity of the obtained polyoxyethylenediacetic acid was 93.1% by weight.

Example 4

Into a 5 liter autoclave, 644 g (0.2 mol) of polyoxyethylenediacetic acid (purity: 93.1% by weight) expressed by formula [13] which was obtained in Example 3, 20.0 g (0.24 mol) of a 48% by weight aqueous solution of sodium hydroxide, and 100 g of ion-exchanged water were placed, and the saponification was conducted in the resultant mixture under a nitrogen atmosphere at 100° C. for 2 hours while the mixture was stirred. Then, water was removed at a decreased pressure of 5 to 30 mmHg at 110°±5° C. for 1 hour. After the temperature was decreased to 70° C., 1,000 g of toluene, 134.6 g (2.4 mol) of potassium hydroxide in flakes and 139.8 g (1.2 mol) of sodium monochloroacetate were added, and the reaction was allowed to proceed at 125°±50° C. for 3 hours.

Then, the temperature was decreased to 80° C., and 200 g of ion-exchanged water was added. After being stirred for 30 minutes, the entire amount of the reaction mixture was transferred into a separation funnel. To the reaction mixture in the separation funnel, 38% by weight hydrochloric acid was slowly added to adjust pH of the reaction mixture to 1.5. Then, 300 g of a 23% aqueous solution of sodium chloride was added, and the obtained mixture was heated to 90° C. while being stirred. After the heated mixture was left standing at 90° C. for 1 hour, a separated aqueous layer was removed. The remaining toluene layer was washed with 500 g of a 23% by weight aqueous solution of sodium chloride 4 times in accordance with the same procedure.

The toluene layer was taken out, and water and the solvent were removed at a decreased pressure of 5 to 30 mmHg at 80°±5° C. while nitrogen gas was blown into the solution. Salts precipitated from the product were removed by filtration with pressure, and 562 g of polyoxyethylenediacetic acid expressed by formula [13]:

$$HOOCCH_2O(C_2H_4O)_{70}CH_2COOH \qquad [13]$$

was obtained. The obtained polyoxyethylenediacetic acid had an acid value of 34.2 (theoretical value: 34.87), a hydroxyl value of 0.8 after correction by the acid value (theoretical value: 0), a conversion of the hydroxyl group into the carboxylic acid of 98.1% as calculated from the acid value, and a saponification value of 34.5 (theoretical value: 34.87).

Figure 4:
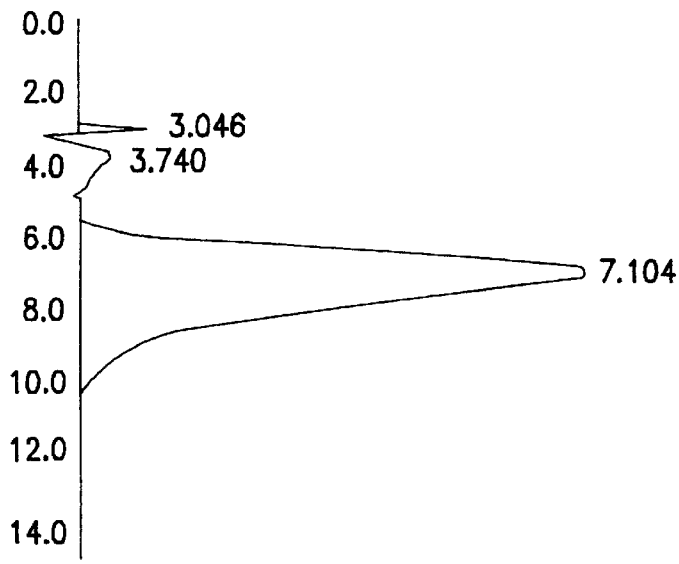
FIG. 4 shows a chromatogram of polyoxyethylenediacetic acid obtained in Example 4.

The chromatogram of polyoxyethylenediacetic acid obtained in accordance with the same method as that used in Example 3 is shown in FIG. 4. It could be confirmed from FIG. 4 that the purity of the obtained polyoxyethylenediacetic acid was 97.3% by weight.

Example 5

Into a 5 liter autoclave, 1,051 g (0.05 mol) of polyoxyethylene monomethyl ether expressed by formula [14]:

$$CH_3O(C_2H_4O)_{477}H \qquad [14]$$

and having an average molecular weight of 21,011 and a hydroxyl value of 2.67 and 1,800 g of toluene were placed, and the resultant mixture was stirred under a nitrogen atmosphere at 50° C. until polyoxyethylene monomethyl ether was completely dissolved. Then, 84.2 g (1.5 mol) of potassium hydroxide in flakes and 140 g (0.8 mol) of sodium β-monobromopropionate were added to the solution. The autoclave was quickly purged with nitrogen and heated to 130° C. The mixture was kept being stirred at 130° C. for 5 hours to allow the reaction to proceed.

Then, removal of water and the solvent was started by decreasing the pressure while the temperature was kept at 130° C. After the pressure inside the autoclave reached 30 mmHg, the autoclave was kept at the same pressure and temperature for 1 hour. The temperature was decreased to 70° C., and 16.8 g (0.3 mol) of potassium hydroxide in flakes, 42 g (0.24 mol) of sodium β-monobromopropionate, and 2,000 g of toluene were added. The autoclave was quickly purged with nitrogen and heated to 130° C. The mixture was kept being stirred at 130° C. for 3 hours to allow the reaction to proceed. The temperature was decreased to 80° C. again, and 11.2 g (0.2 mol) of potassium hydroxide in flakes and 28.0 g (0.16 mol) of sodium β-monobromopropionate were added. The autoclave was quickly purged with nitrogen and heated to 130° C. The mixture was kept being stirred at 130° C. for 3 hours to allow the reaction to proceed. The temperature was decreased to 80° C. again, and 11.2 g (0.2 mol) of potassium hydroxide in flakes and 28.0 g (0.16 mol) of sodium β-monobromopropionate were added. The autoclave was quickly purged with nitrogen and heated to 130° C. The mixture was kept being stirred at 130° C. for 3 hours to allow the reaction to proceed. The temperature was decreased to 80° C. again, and 11.2 g (0.2 mol) of potassium hydroxide in flakes and 28.0 g (0.16 mol) of sodium β-monobromopropionate were added. The autoclave was quickly purged with nitrogen and heated to 130° C. The mixture was kept being stirred at 130° C. for 3 hours to allow the reaction to proceed.

Then, the temperature was decreased to 80° C., and 500 g of ion-exchanged water was added. After being stirred for 30 minutes, the entire amount of the reaction mixture was transferred into a separation funnel. To the reaction mixture in the separation funnel, 38% by weight hydrochloric acid was slowly added to adjust pH of the reaction mixture to 1.2. Then, 700 g of a 23% aqueous solution of sodium chloride was added, and the obtained mixture was heated to 90° C. while being stirred. After the heated mixture was left standing at 90° C. for 1 hour, a separated aqueous layer was removed. The remaining toluene layer was washed with 700 g of a 23% by weight aqueous solution of sodium chloride 4 times in accordance with the same procedure.

The toluene layer was taken out, and water and the solvent were removed at a decreased pressure of 5 to 30 mmHg at 80°±5° C. while nitrogen gas was blown into the solution. Salts precipitated from the product were removed by filtration with pressure, and 830 g of methoxypolyoxyethylenepropionic acid expressed by formula [15]:

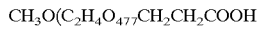

CH$_3$O(C$_2$H$_4$O)$_{477}$CH$_2$CH$_2$COOH     [15]

was obtained.

Into a 5 liter autoclave, 422 g (0.02 mol) of methoxypolyoxyethylenepropionic acid expressed by formula [15] which was obtained above, 2 g (0.024 mol) of a 48% by weight aqueous solution of sodium hydroxide, and 50 g of ion-exchanged water were placed, and the resultant mixture was stirred under a nitrogen atmosphere at 100° C. for 2 hours for saponification. Then, water was removed at a decreased pressure of 5 to 30 mmHg at 110°±5° C. for 1 hour. After, the temperature was decreased to 70° C., 1,200 g of toluene, 11.2 g (0.2 mol) of potassium hydroxide in flakes and 24.5 g (0.14 mol) of sodium β-monobromopropionate were added, and the reaction was allowed to proceed at 130° C. for 3 hours.

Then, the temperature was decreased to 80° C., and 100 g of ion-exchanged water was added. After being stirred for 30 minutes, the entire amount of the reaction mixture was transferred into a separation funnel. To the reaction mixture in the separation funnel, 38% by weight hydrochloric acid was slowly added to adjust pH of the reaction mixture to 1.5. Then, 300 g of a 23% aqueous solution of sodium chloride was added, and the obtained mixture was heated to 90° C. while being stirred. After the heated mixture was left standing at 90° C. for 1 hour, a separated aqueous layer was removed. The remaining toluene layer was washed with 300 g of a 23% by weight aqueous solution of sodium chloride 4 times in accordance with the same procedure.

The toluene layer was taken out, and water and the solvent were removed at a decreased pressure of 5 to 30 mmHg at 80°±5° C. while nitrogen gas was blown into the solution. Salts precipitated from the product were removed by filtration with pressure, and 342 g of methoxypolyoxyethylenepropionic acid expressed by formula [15]:

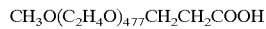

CH$_3$O(C$_2$H$_4$O)$_{477}$CH$_2$CH$_2$COOH     [15]

was obtained. The obtained methoxypolyoxyethylenepropionic acid had an acid value of 2.32 (theoretical value: 2.66), a hydroxyl value of 0.1 after correction by the acid value (theoretical value: 0), a conversion of the hydroxyl group into the carboxylic acid of 89.2% as calculated from the acid value, and a saponification value of 2.40 (theoretical value: 2.66).

Figure 5:
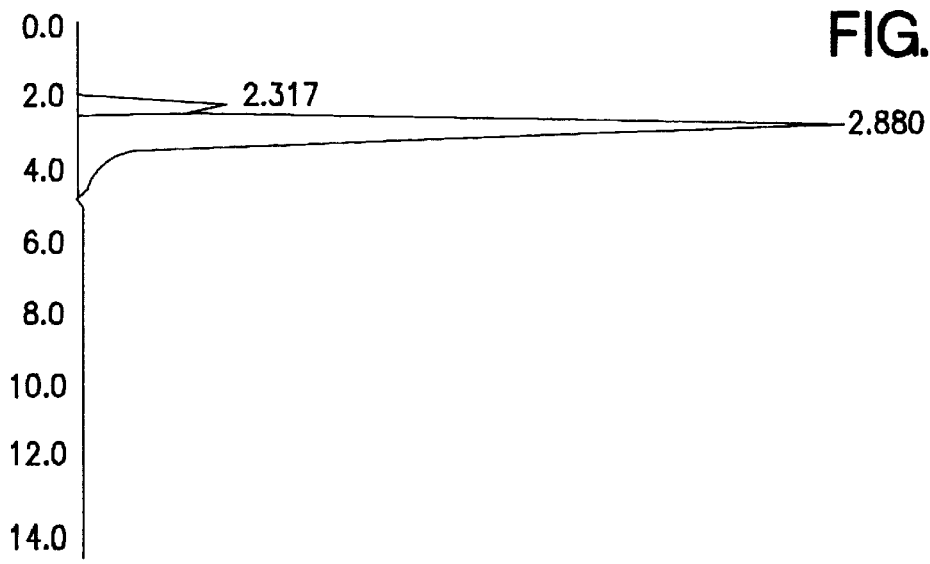
FIG. 5 shows a chromatogram of methoxypolyoxyethylenepropionic acid obtained in Example 5.

The chromatogram of methoxypolyoxyethylenepropionic acid obtained in accordance with the same method as that used in Example 1 is shown in FIG. 5. It could be confirmed from FIG. 5 that the purity of the obtained methoxypolyoxyethylenepropionic acid was 88.6% by weight.

Comparative Example 1

Into a 5 liter autoclave, 1,240 g (0.4 mol) of polyoxyethylene glycol expressed by formula [12]:

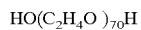

HO(C$_2$H$_4$O )$_{70}$H     [12]

and having an average molecular weight of 3,100 and a hydroxyl value of 36.2 and 56 g (0.48 mol) of sodium monochloroacetate were placed.

After the autoclave was purged with nitrogen, 70 g (0.84 mol) of a 48% by weight aqueous solution of sodium hydroxide was added dropwise at 60° C. during 2 hours. While the aqueous solution of sodium hydroxide was added, the temperature and the pressure inside the autoclave were kept at 60° C. and 20 mmHg or less, respectively, and water in the aqueous solution of sodium hydroxide and water formed by the reaction were condensed into a cooled trap and removed to the outside of the reaction system. After the addition had been completed, the reaction was allowed to continue at 60° C. for additional 1 hour. Then, 1,000 g of toluene was added to the reaction mixture, and the resultant mixture was kept being stirred for 10 minutes. The entire amount of the reaction mixture was transferred into a separation funnel, and pH of the reaction mixture was adjusted to 1.5 by adding a 38% by weight hydrochloric acid. Then, the obtained mixture was heated to 90° C. After the heated mixture was left standing at 90° C. for 1 hour, a separated aqueous lower layer was removed. The upper layer was transferred to a Kjeldahl flask and dehydrated at 70° C. at a decreased pressure of 30 mmHg or less for 2 hours. Salts precipitated from the product were removed by filtration with pressure, and 1,042 g of polyoxyethylenediacetic acid expressed by formula [13]:

$$HOOCCH_2O(C_2H_4O)_{70}CH_2COOH \quad [13]$$

was obtained. The obtained polyoxyethylenediacetic acid had an acid value of 15.4 (theoretical value: 34.87), a hydroxyl value of 22.0 after correction by the acid value (theoretical value: 0), a conversion of the hydroxyl group into the carboxylic acid of 44.1% as calculated from the acid value, and a saponification value of 17.8 (theoretical value: 34.87).

Figure 6:
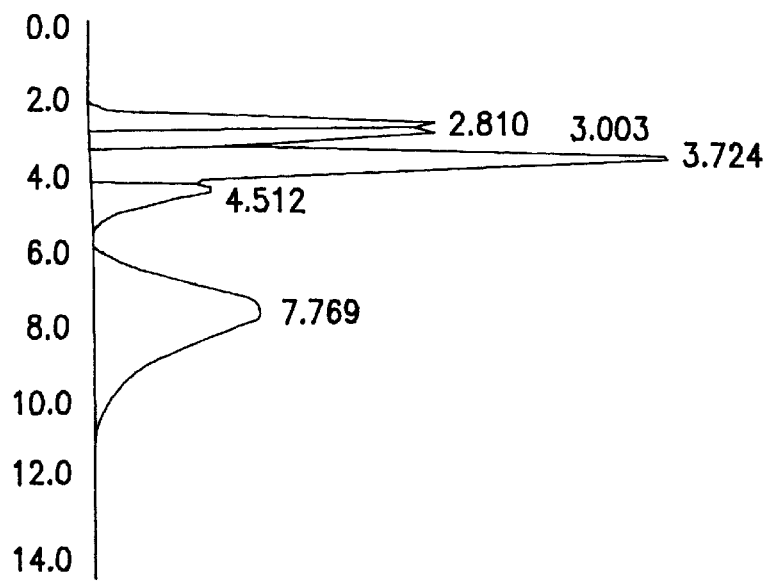
FIG. 6 shows a chromatogram of polyoxyethylenediacetic acid obtained in Comparative Example 1.

The chromatogram obtained in accordance with the same method as that used in Example 3 is shown in FIG. 6. In the chromatogram shown in FIG. 6, the peak at the retention time of 3.72 minute is assigned to polyethylene glycol expressed by formula [12], and the peak at the retention time of 7.77 minutes is assigned to polyoxyethylenediacetic acid expressed by formula [13]. In addition to these peaks, three other peaks are found in the chromatogram shown in FIG. 6, and it can be understood that byproducts other than the starting material and the object product are present. The purity of the obtained polyoxyethylenediacetic acid was found to be 36.8% by weight which is markedly different from the value calculated from the acid value. This result is considered to have been obtained because the number of repeated washing of the product was insufficient, and hydrochloric acid used for adjustment of pH remained in the product.

Comparative Example 2

Into a 5 liter autoclave, 1,240 g (0.4 mol) of polyoxyethylene glycol expressed by formula [12]:

$$HO(C_2H_4O)_{70}H \quad [12]$$

and having an average molecular weight of 3,100 and a hydroxyl value of 36.2 and 400 g of xylene were placed, and the resultant mixture was stirred under a nitrogen atmosphere at 70° C. until polyethylene glycol was completely dissolved. After the temperature was increased to 90° C., 19.2 g (0.4 mol) of sodium hydroxide in granules and 56 g (0.48 mol) of sodium monochloroacetate were added in 5 separate equal portions every hour. The reaction was allowed to proceed during the addition while the reaction system was stirred. After the entire amount had been added, the reaction was continued for additional one hour.

After the reaction had been completed, the entire amount of the reaction mixture was transferred into a separation funnel. To the reaction mixture in the separation funnel, 10% by weight hydrochloric acid was added to adjust pH of the reaction mixture to 1.5. Then, the mixture was heated to 90° C. while being stirred, and the heated mixture was left standing at 90° C. for 1 hour. Because the mixture was not separated into two layers even after 1 hour, 600 g of xylene was added while the mixture was stirred, and the resultant mixture was left standing at 90° C. Then, the aqueous lower layer was removed. The remaining upper layer was transferred to a Kjeldahl flask and dehydrated at 70° C. at a decreased pressure of 30 mmHg or less for 2 hours. Salts precipitated from the product were removed by filtration with pressure, and 1,042 g of polyoxyethylenediacetic acid expressed by formula [13]:

$$HOOCCH_2O(C_2H_4O)_{70}CH_2COOH \quad [13]$$

was obtained. The obtained polyoxyethylenediacetic acid had an acid value of 26.0 (theoretical value: 34.87), a hydroxyl value of 11.5 after correction by the acid value (theoretical value: 0), a conversion of the hydroxyl group into the carboxylic acid of 74.6% as calculated from the acid value, and a saponification value of 24.2 (theoretical value: 34.8).

Figure 7:
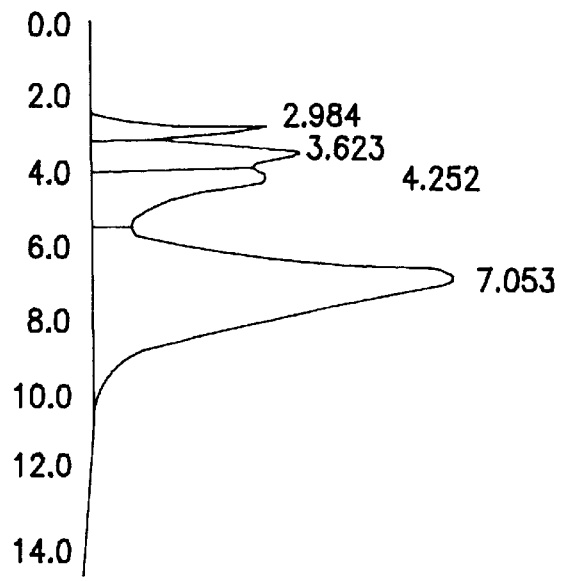
FIG. 7 shows a chromatogram of polyoxyethylenediacetic acid obtained in Comparative Example 2.

The chromatogram of polyoxyethylenediacetic obtained in accordance with the same method as that used in Example 3 is shown in FIG. 7. It could be confirmed from FIG. 7 that the purity of the obtained polyoxyethylenediacetic acid was 68.1% by weight.

The reaction conditions and the results in Examples 1 to 7 and Comparative Examples 1 and 2 are summarized in Tables 1 and 2, respectively.

TABLE 1-1

| | | salt of halogenated carboxylic acid | |
|---|---|---|---|
| | polyoxyalkylene compound | type | amount (ratio by mol) |
| Example 1 | $CH_3O[(C_2H_4O)_{38}(C_3H_6O)_5]H$ | $ClCH_2COONa$ | 6.0 |
| Example 2 | $CH_3O(C_2H_4O)_{113}H$ | $ClCH_2COONa$ | 10.1 |
| Example 3 | $HO(C_2H_4O)_{70}H$ | $ClCH_2COONa$ | 17.6 |
| Example 4 | $HO(C_2H_4O)_{70}H$ | $ClCH_2COONa$ | 23.6 |
| Example 5 | $CH_3O(C_2H_4O)_{47.7}H$ | $BrCH_2CH_2COONa$ | 30.4 |
| Comparative Example 1 | $HO(C_2H_4O)_{70}H$ | $ClCH_2COONa$ | 1.2 |
| Comparative Example 2 | $HO(C_2H_4O)_{70}H$ | $ClCH_2COONa$ | 1.2 |

TABLE 1-2

| | alkali metal hydroxide | | reaction temperature (°C.) | organic solvent |
|---|---|---|---|---|
| | type | amount (ratio by mol) | | |
| Example 1 | KOH in flakes | 18.0 | 120 | toluene |
| Example 2 | KOH in flakes | 40.8 | 120 | xylene |
| Example 3 | NaOH in granules | 37.25 | 130 | toluene |
| Example 4 | KOH in flakes | 49.25 | 125 | toluene |
| Example 5 | KOH in flakes | 48.0 | 130 | toluene |
| Comparative Example 1 | aq. soln. of NaOH | 2.1 | 60 | none |
| Comparative Example 2 | NaOH in granules | 1.2 | 70 | xylene |

TABLE 2

| | acid value | hydroxyl value | conversion to carboxylic acid (%) | purity (% by wt.) |
|---|---|---|---|---|
| Example 1 | 23.3 | 3.8 | 85.7 | 84.7 |
| Example 2 | 10.4 | 0.6 | 93.9 | 93.8 |
| Example 3 | 32.8 | 2.0 | 94.0 | 93.1 |
| Example 4 | 34.2 | 0.8 | 98.1 | 97.3 |
| Example 5 | 2.32 | 0.1 | 89.2 | 88.6 |
| Comparative Example 1 | 15.4 | 22.0 | 44.1 | 36.8 |
| Comparative Example 2 | 26.0 | 11.5 | 74.6 | 68.1 |

It is clearly understood from the results in Tables 1 and 2 that a high purity, high molecular weight polyoxyalkylenecarboxylic acid can easily be obtained in accordance with the process of the present invention.

What is claimed is:

1. A process for producing a polyoxyalkylenecarboxylic acid represented by any of general formulae [6] and [7]:

$$\begin{array}{c} O(C_2H_4O)_a(AO)_b(CH_2)_m COOH \\ | \\ Z \\ | \\ O(C_2H_4O)_c(AO)_d(CH_2)_m COOH \end{array} \quad [6]$$

$$\begin{array}{c} O(C_2H_4O)_a(AO)_b(CH_2)_m COOH \\ | \\ Z \\ | \\ O(C_2H_4O)_c(AO)_d R^1 \end{array} \quad [7]$$

which comprises:

(A) a step of obtaining a salt of a polyoxyalkylenecarboxylic acid represented by any of general formulae [4] and [5]:

$$\begin{array}{c} O(C_2H_4O)_a(AO)_b(CH_2)_m COOM \\ | \\ Z \\ | \\ O(C_2H_4O)_c(AO)_d(CH_2)_m COOM \end{array} \quad [4]$$

$$\begin{array}{c} O(C_2H_4O)_a(AO)_b(CH_2)_m COOM \\ | \\ Z \\ | \\ O(C_2H_4O)_c(AO)_d R^1 \end{array} \quad [5]$$

by reacting a polyoxyalkylene compound represented by any of general formulae [1] and [2]:

$$\begin{array}{c} O(C_2H_4O)_a(AO)_b H \\ | \\ Z \\ | \\ O(C_2H_4O)_c(AO)_d H \end{array} \quad [1]$$

$$\begin{array}{c} O(C_2H_4O)_a(AO)_b H \\ | \\ Z \\ | \\ O(C_2H_4O)_c(AO)_d R^1 \end{array} \quad [2]$$

with a salt of a halogenated carboxylic acid represented by general formula [3]:

$$X(CH_2)_m COOM \quad [3]$$

in an amount of 4 to 50 mol per 1 mol of the polyoxyalkylene compound and an alkali metal hydroxide in an amount of 8 to 70 mol per 1 mol of the polyoxyalkylene compound in the presence of an organic solvent in an amount by weight 0.5 to 4 times an amount by weight of the polyoxyalkylene compound at 80° to 150° C.;

(B) a step of converting the obtained salt of a polyoxyalkylenecarboxylic acid into the polyoxyalkylenecarboxylic acid by adjusting pH of the reaction mixture obtained in step (A) to 3 or less by adding an inorganic acid;

(C) a step of removing unreacted raw materials, byproducts, and the inorganic acid and the salt in excess amounts from the solution containing the polyoxyalkylenecarboxylic acid which is obtained in step (B) by washing with a 1 to 30% by weight aqueous solution of an inorganic salt 1 to 5 times at 60° to 120° C.; and (D) a step of removing the organic solvent and water from the solution obtained in step (C) at a decreased pressure at 50° to 120° C. and removing precipitated salts by filtration;

wherein, in general formulae [1] to [7], $R^1$ represents a hydrocarbon group having 1 to 4 carbon atoms; Z represents ethylene group, propylene group, or trimethylene group; AO represents an oxyalkylene group having 3 or 4 carbon atoms; a and c each represents an average number of addition of oxyethylene group, and a+c=40 to 1,000; b and d each represents an average number of addition of an oxyalkylene group having 3 or 4 carbon atoms, and b+d=0 to 100; (b+d)/(a+b+c+d)≦0.5; when b+d is 2 or more, oxyethylene group and the oxyalkylene group having 3 or 4 carbon atoms are arranged in a random order or in blocks; X represents chlorine or bromine; m represents 1 or 2; and M represents sodium or potassium.

2. A process according to claim 1, wherein, after step (A) has been completed, step (E) is conducted in which the organic solvent and water are removed from the reaction mixture obtained in step (A) at a decreased pressure, the solvent is added again to a resultant reaction mixture, and the reaction is allowed to proceed in the obtained solution at 100° to 150° C.; and step (B) is conducted using a product of step (E) in place of the reaction mixture obtained in step (A).

3. A process according to claim 1, wherein, after step (A) or step (E) has been completed, step (F) is conducted in which the salt of a halogenated carboxylic acid represented by general formula [3] and the alkali metal hydroxide are added to a reaction mixture obtained in step (A) or step (E), amounts by weight of the salt of a halogenated carboxylic acid and the alkali metal hydroxide being 0.1 to 0.5 times the amounts by weight of the respective compounds used in step (A), the reaction is allowed to proceed, and this procedure is repeated 1 to 6 times; and step (B) is conducted using a product of step (F) in place of the reaction mixture obtained in step (A).

4. A process according to claim 2, wherein, after step (A) or step (E) has been completed, step (F) is conducted in which the salt of a halogenated carboxylic acid represented by general formula [3] and the alkali metal hydroxide are added to a reaction mixture obtained in step (A) or step (E), amounts by weight of the salt of a halogenated carboxylic acid and the alkali metal hydroxide being 0.1 to 0.5 times the amounts by weight of the respective compounds used in step (A), the reaction is allowed to proceed, and this procedure is repeated 1 to 6 times; and step (B) is conducted using a product of step (F) in place of the reaction mixture obtained in step (A).

5. A process according to claim 1, wherein, after step (D) has been completed, a step is conducted in which an aqueous solution of the alkali metal hydroxide in an amount by mol 1 to 2 times the amount by mol of carboxyl group in the polyoxyalkylenecarboxylic acid is added to the product of step (D), the obtained solution is heated to 50° to 150° C., water is removed from the solution at 50° to 150° C. at a decreased pressure, the salt of a halogenated carboxylic acid, the alkali metal hydroxide, and the organic solvent are added, an amount by mol of the salt of a halogenated carboxylic acid being 0.5 to 10 times the amount by mol of the polyoxyalkylenecarboxylic acid, an amount by mol of the alkali metal hydroxide being 1 to 20 times the amount by mol of the polyoxyalkylenecarboxylic acid, and an amount by weight of the organic solvent being 0.5 to 4 times the amount by weight of the polyoxyalkylenecarboxylic acid, and the reaction is allowed to proceed at 100° to 150° C.; and then steps (B), (C), and (D) are conducted again using a reaction mixture obtained in this step in place of the reaction mixture obtained in step (A).

6. A process according to claim 2, wherein, after step (D) has been completed, a step is conducted in which an aqueous solution of the alkali metal hydroxide in an amount by mol 1 to 2 times the amount by mol of carboxyl group in the polyoxyalkylenecarboxylic acid is added to the product of step (D), the obtained solution is heated to 50° to 150° C., water is removed from the solution at 50° to 150° C. at a decreased pressure, the salt of a halogenated carboxylic acid, the alkali metal hydroxide, and the organic solvent are added, an amount by mol of the salt of a halogenated carboxylic acid being 0.5 to 10 times the amount by mol of the polyoxyalkylenecarboxylic acid, an amount by mol of the alkali metal hydroxide being 1 to 20 times the amount by mol of the polyoxyalkylenecarboxylic acid, and an amount by weight of the organic solvent being 0.5 to 4 times the amount by weight of the polyoxyalkylenecarboxylic acid, and the reaction is allowed to proceed at 100° to 150° C.; and then steps (B), (C), and (D) are conducted again using a reaction mixture obtained in this step in place of the reaction mixture obtained in step (A).

7. A process according to claim 3, wherein, after step (D) has been completed, a step is conducted in which an aqueous solution of the alkali metal hydroxide in an amount by mol 1 to 2 times the amount by mol of carboxyl group in the polyoxyalkylenecarboxylic acid is added to the product of step (D), the obtained solution is heated to 50° to 150° C., water is removed from the solution at 50° to 150° C. at a decreased pressure, the salt of a halogenated carboxylic acid, the alkali metal hydroxide, and the organic solvent are added, an amount by mol of the salt of a halogenated carboxylic acid being 0.5 to 10 times the amount by mol of the polyoxyalkylenecarboxylic acid, an amount by mol of the alkali metal hydroxide being 1 to 20 times the amount by mol of the polyoxyalkylenecarboxylic acid, and an amount by weight of the organic solvent being 0.5 to 4 times the amount by weight of the polyoxyalkylenecarboxylic acid, and the reaction is allowed to proceed at 100° to 150° C.; and then steps (B), (C), and (D) are conducted again using a reaction mixture obtained in this step in place of the reaction mixture obtained in step (A).

8. A process according to claim 4, wherein, after step (D) has been completed, a step is conducted in which an aqueous solution of the alkali metal hydroxide in an amount by mol 1 to 2 times the amount by mol of carboxyl group in the polyoxyalkylenecarboxylic acid is added to the product of step (D), the obtained solution is heated to 50° to 150°0. C., water is removed from the solution at 50° to 150° C. at a decreased pressure, the salt of a halogenated carboxylic acid, the alkali metal hydroxide, and the organic solvent are added, an amount by mol of the salt of a halogenated carboxylic acid being 0.5 to 10 times the amount by mol of the polyoxyalkylenecarboxylic acid, an amount by mol of the alkali metal hydroxide being 1 to 20 times the amount by mol of the polyoxyalkylenecarboxylic acid, and an amount by weight of the organic solvent being 0.5 to 4 times the amount by weight of the polyoxyalkylenecarboxylic acid, and the reaction is allowed to proceed at 100° to 150° C.; and then steps (B), (C), and (D) are conducted again using a reaction mixture obtained in this step in place of the reaction mixture obtained in step (A).

9. A process according to claim 1, wherein the alkali metal hydroxide is sodium hydroxide or potassium hydroxide.

10. A process according to claim 1, wherein the organic solvent is toluene or xylene.

11. A process according to claim 1, wherein the aqueous solution of an inorganic salt is an aqueous solution of sodium chloride, potassium chloride, sodium sulfate, or magnesium sulfate.

\* \* \* \* \*